United States Patent [19]

Findeisen

[11] Patent Number: 4,470,932
[45] Date of Patent: Sep. 11, 1984

[54] PREPARATION OF CARBOXYLIC ACID ANHYDRIDES

[75] Inventor: Kurt Findeisen, Odenthal, Fed. Rep. of Germany

[73] Assignee: Bayer Aktiengesellschaft, Leverkusen, Fed. Rep. of Germany

[21] Appl. No.: 436,093

[22] Filed: Oct. 22, 1982

[30] Foreign Application Priority Data

Nov. 11, 1981 [DE] Fed. Rep. of Germany ....... 3144791

[51] Int. Cl.³ .................... C07C 51/54; C07C 51/56
[52] U.S. Cl. ................. 260/546; 260/548;
544/87; 544/130; 544/132; 544/133; 544/137;
544/139; 544/140; 544/152; 546/199; 546/209;
546/210; 546/211; 546/214; 548/123; 548/236;
548/255; 548/262; 548/343; 548/378; 548/454;
548/467; 548/492; 548/517; 548/518; 548/531;
549/473; 549/484
[58] Field of Search ............... 260/546, 548; 549/473,
549/484; 544/87, 130, 132, 133, 137, 139, 140,
152; 546/199, 209, 210, 211, 214; 548/123, 236,
255, 262, 343, 378, 454, 467, 492, 517, 518, 531

[56] References Cited

FOREIGN PATENT DOCUMENTS 171146 5/1906 Fed. Rep. of Germany.
394730 5/1924 Fed. Rep. of Germany.

OTHER PUBLICATIONS

Journal of The Chemical Society, Perkin Transactions I, 1976, pp. 564–569.
Chemical Abstracts, vol. 62, 1965, p. 2700.
Hartke et al. article-Archiv der Pharmazie, vol. 303, Aug. 1970, No. 8, (5 pp.); (Exhibit A).
Translation of extract from publication by Hartke et al. in above publication (p. 632, lines 7–14, (Exhibit A), Comparative Test, (Exhibit B).
Organosilicon Compounds, 1965-Vladimir Baäzant, Václav Chvalovsky, Jiri Rathousky, Publishing House of the Czechoslovak Academy of Sciences Prague.

*Primary Examiner*—Richard Raymond
*Attorney, Agent, or Firm*—Sprung, Horn, Kramer & Woods

[57] ABSTRACT

Carboxylic acid anhydrides of the general formula $$R-CO-O-CO-R' \qquad (I)$$

in which
  R and R' are identical or different and represent an optionally substituted alkyl group having 1 to 18 carbon atoms, an optionally substituted cycloalkyl group having 3 to 12 carbon atoms or an optionally substituted aryl group, or represent an optionally substituted 5-membered or 6-membered heterocyclic radical which additionally can be fused to a benzene ring, are obtained in high yields by a process in which a trimethylsilyl carboxylate of the general formula $$R-CO-OSi(CH_3)_3 \qquad (II)$$

in which
  R has the meaning given above, is reacted with a carboxylic acid-halide of the general formula $$R'CO-X \qquad (III)$$

in which
  R' has the meaning given above, and
  X represents a halogen atom, if appropriate in the presence of a catalyst and, if appropriate, in the presence of a diluent, at a temperature between 20° and 250° C.

The carboxylic acid anhydrides are valuable intermediate products for organic syntheses. They can be used, for example, for the preparation of certain herbicidally active compounds.

13 Claims, No Drawings

PREPARATION OF CARBOXYLIC ACID ANHYDRIDES

The present invention relates to an unobvious process for the preparation of certain carboxylic acid anhydrides. The process according to the invention allows carboxylic acid anhydrides to be prepared from the trimethylsilyl esters of the corresponding carboxylic acids.

Numerous methods for the synthesis of carboxylic acid anhydrides have already been described in the literature (see for example, Houben-Weyl, Methoden der Organischen Chemie (Methods of Organic Chemistry), 4th Edition, Volume VIII, pages 476–480 (1952)). However, no process which permits the conversion of the trimethylsilyl esters of carboxylic acids directly into the corresponding anhydrides has hitherto been disclosed.

The present invention now provides a process for the production of a carboxylic acid anhydride of the general formula

in which
R and R' are identical or different and represent an optionally substituted alkyl group having 1 to 18 carbon atoms, an optionally substituted cycloalkyl group having 3 to 12 carbon atoms or an optionally substituted aryl group, or represent an optionally substituted 5-membered or 6-membered heterocyclic radical which additionally can be fused to a benzene ring,
characterized in that a trimethylsilyl carboxylate of the general formula

in which
R has the meaning given above, is reacted with a carboxylic acid-halide of the general formula

in which
R' has the meaning given above, and
X represents a halogen atom,
if appropriate in the presence of a catalyst and, if appropriate, in the presence of a diluent, at a temperature between 20° C. and 250° C.

The process according to the invention allows carboxylic acid anhydrides of formula (I) to be obtained in very high yield and purity.

In the reaction according to the invention, the equivalent amount of trimethylsilyl halide of the formula

wherein
X represents a halogen atom, is formed simultaneously.

It is particularly surprising that carboxylic acid anhydrides of the formula (I) are obtainable in high yield and purity by the process according to the invention, since, in view of the prior art, it was to be expected that this reaction would not take place at all, since trimethylsilyl chloride reacts with carboxylic acid anhydrides—in a reaction which is the reverse of that according to the invention—with the formation of the corresponding trimethylsilyl carboxylates and carboxylic acid-chlorides (see Organosilicon Compounds I, page 62 (1965)).

The process according to the invention possesses a number of advantages. Thus, it is not restricted to the synthesis of a few particular compounds but can be very widely applied, and can be carried out in a one-pot reaction. The process gives carboxylic acid anhydrides in virtually quantitative yield and excellent purity, free of troublesome or pollutant by-products. An additional decisive advantage of the process according to the invention is the fact that the working-up presents no problems; the working-up is effected most simply and advantageously by distillation and recrystallization. The trimethylsilyl halide formed in the course of the reaction is in every case distilled off. In a preferred embodiment, the trimethylsilyl halide formed in the course of the reaction is distilled off continuously from the reaction mixture, at the rate at which it is formed.

If trimethylsilyl benzoate and benzoyl chloride are used as starting materials, the course of the reaction according to the invention is illustrated by the following equation:

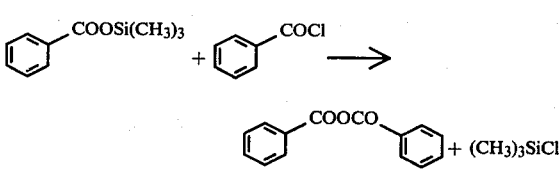

Trimethylsilyl carboxylates of formula (II) used as starting materials, and carboxylic acid-halides of formula (III) are known and can be synthesized according to known methods (see Organosilicon Compounds. I, page 61 (1965); Organikum, 1967, page 409).

In starting materials of formulae (II) and (III), R and R', respectively, preferably independently represent a straight-chain or a branched alkyl group having 1 to 4 carbon atoms, and being optionally substituted by a substituent selected from alkoxy having 1 to 4 carbon atoms, carbalkoxy having 1 to 4 carbon atoms in the alkoxy group, nitro, cyano and halogen (such as fluorine, chlorine, bromine or iodine); a cycloalkyl group which is optionally substituted by a substituent selected from alkyl, alkoxy, or carbalkoxy, each having up to 4 carbon atoms, nitro, cyano and halogen (such as, for example, fluorine, chlorine and bromine), and which has 5 or 6 carbon atoms in the ring system; an aryl group, in particular phenyl or naphthyl group, which is optionally substituted by a substituent selected from alkyl, alkoxy, or carbalkoxy, each having up to 4 carbon atoms, nitro and halogen (such as, for example, fluorine, chlorine and bromine); or a 5-membered or 6-membered heterocyclic radical which is optionally substituted by a substituent selected from alkyl, alkoxy or carbalkoxy, each having up to 4 carbon atoms, nitro, cyano, and halogen (such as, for example, fluorine, chlorine and bromine), and which can contain 1 to 3 hetero atoms (such as oxygen, sulphur and/or nitrogen) in the ring and additionally can be fused to a benzene ring.

The following may be mentioned as examples of particularly suitable heterocyclic radicals: morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

The following may be mentioned individually as preferred trimethylsilyl carboxylates of the formula (II): trimethylsilyl acetate, trimethylsilyl propionate, trimethylsilyl butyrate, trimethylsilyl pivaloate, trimethylsilyl hexanecarboxylate, trimethylsilyl dodecanecarboxylate, trimethylsilyl palmitate, trimethylsilyl stearate, trimethylsilyl α-(2-[2,2-dichlorovinyl]-3,3-dimethyl-cyclopropan-1-yl)-α-carboxylate, trimethylsilyl cyclopropanecarboxylate, trimethylsilyl methylcyclopropanecarboxylate, trimethylsilyl cyclobutanecarboxylate, trimethylsilyl methylcyclobutanecarboxylate, trimethylsilyl cyclopentanecarboxylate, trimethylsilyl cyclohexanecarboxylate, trimethylsilyl benzoate, trimethylsilyl chlorobenzoate, trimethylsilyl dichlorobenzoate, trimethylsilyl trifluoromethylbenzoate, trimethylsilyl trifluoromethoxybenzoate, trimethylsilyl naphthalene-1-carboxylate, trimethylsilyl 1-phenyl-pyrazol-5-one-3-carboxylate, trimethylsilyl terephthalate and trimethylsilyl isophthalate.

Trimethylsilyl benzoate and trimethylsilyl pivaloate are particularly preferred.

The following may be mentioned individually as preferred carboxylic-acid halides according to formula (III): acetyl chloride, acetyl bromide, propionyl chloride, propionyl bromide, butyric acid-chloride, pivaloyl chloride, hexanecarboxylic acid-chloride, dodecanecarboxylic acid-chloride, palmitic acid-chloride, stearic acid-chloride, cyclopropanecarboxylic acid-chloride, methylcyclopropanecarboxylic acid-chloride, α-(2-[2,2-dichlorovinyl]-3,3-dimethylcyclopropan-1-yl)-α-carboxylic acid-chloride, cyclobutanecarboxylic acid-chloride, methylcyclobutanecarboxylic acid-chloride, cyclopentanecarboxylic acid-chloride, cyclohexanecarboxylic acid-chloride, benzoyl chloride, benzoyl fluoride, chlorobenzoyl chloride, dichlorobenzoyl chloride, trifluoromethylbenzoyl chloride, trifluoromethylbenzoyl fluoride, trifluoromethoxybenzoyl chloride, naphthalene-1-carboxylic acid-chloride, 1-phenyl-pyrazol-5-one-3-carboxylic acid-chloride, terephthalic acid-dichloride and isophthalic acid-dichloride. Benzoyl chloride and pivaloyl chloride are particularly preferred.

Preferably the fluorides, and particularly preferably the chlorides, are used as carboxylic acid-halides.

Diluents which can be employed in carrying out the process according to the invention are any of the inert organic solvents which do not undergo chemical reactions either with the carboxylic acid-halides of the formula (III) or with the trimethylsilyl carboxylates of the formula (II) and the carboxylic acid anhydrides of the formula (I). Examples of such solvents are the xylenes (such as o-xylene), chlorobenzene, o-dichlorobenzene, the trichlorobenzenes, nitrobenzene and tetramethylenesulphone. In general, however, the reaction according to the invention is carried out without a diluent.

The reaction temperature can be varied within the stated relatively wide range of 20° C. and 250° C., preferably between 50° C. and 200° C.

The reaction can be accelerated by the addition of catalytic amounts of a Lewis acid.

The following may be mentioned as a suitable Lewis acid: zinc chloride, zinc cyanide, copper cyanide, iron-(III) chloride, aluminum chloride, boron trifluoride, boron trifluoride etherate, triethylammonium fluoride or triethylammonium fluoride.2HF.

The working-up is effected after the end of the reaction, customarily by distillation of the carboxylic acid anhydrides synthesized according to the invention, further purification is unnecessary.

The mixture of the trimethylsilyl carboxylate and the carboxylic acid-halide can also be reacted according to the invention in the gas phase.

In a particular process variant, the reaction according to the invention can also be carried out continuously.

Carboxylic acid anhydrides are frequently used as substitute chemicals for carboxylic acid-chlorides which have a comparable chemical reactivity, but they do not cause the corrosion which occurs when acid-chlorides are used. It is also possible to use carboxylic acid anhydrides as intermediate products for active compounds in plant protection: for example, the carboxylic acid anhydrides(I) can be used as starting materials for the preparation of acyl cyanides (see, for example, DE-OS (German Published Specification) No. 2,614,240, U.S. Pat. No. 4,238,412, DE-OS (German Published Specification) No. 2,642,140, and DE-OS (German Published Specification) No. 2,642,199); the acyl cyanides can in turn be employed as intermediate products for the synthesis of 1,2,4-triazin-5-ones, compounds with outstanding herbicidal properties (see, for example, DE-OS (German Published Specification) No. 2,733,180, DE-OS (German Published Specification) No. 3,003,541, U.S. Pat. No. 4,315,094, U.S. Ser. No. 222,222 filed on Jan. 2, 1981, now pending, and U.S. Ser. No. 235,496 filed on Jan. 19, 1981, now pending). Thus, for example, benzoic acide anhydride can be converted into the herbicidally active compound 3-methyl-4-amino-6-phenyl-1,2,4-triazin-5-one (common name: metamitrone) by a known process in which, in a first stage, benzoic anhydride is converted into benzoyl cyanide by reaction with alkali metal cyanides or anhydrous hydrocyanic acid, and, in a second stage, the benzoyl cyanide is reacted with ethanol in the presence of concentrated hydrochloric acid, and, in a third stage, the resulting ethyl phenylglyoxylate is brought to reaction with acetylhydrazine, and the 1-(phenyl-glyoxylic acid ethyl ester)-2-acetylhydrazone formed is converted in a fourth step with hydrazine hydrate in the presence of pyridine into the abovementioned end product (see, for example, DE-OS (German Published Specification) No. 2,224,161, DE-OS (German Published Specification) No. 2,614,240 and U.S. Pat. No. 4,315,094).

Using processes which are likewise known, pivalic anhydride can be converted into the herbicidally active compound 3-methylthio-4-amino-6-tert.-butyl-1,2,4-triazin-5-one (common name: metribuzin) (see, for example DE-OS (German Published Specification) No. 2,614,240 and U.S. Pat. No. 4,315,094 in association, for example, with U.S. Ser. No. 235,496 filed on Jan. 19, 1981, now pending).

The examples which follow illustrate the invention further.

PREPARATIVE EXAMPLES

EXAMPLE 1

Benzoic anhydride 97 g of trimethylsilyl benzoate (0.5 mol) were warmed to 120°–140° C. in a 250 ml three-necked flask, and 70.3 of benzoyl chloride (0.5 mol) were then added dropwise in the course of 30 minutes. The trimethylsilyl chloride formed was distilled off simultaneously. The residue obtained was pure benzoic anhydride. Yield: 112 g ($\cong$99% of theory) of benzoic anhydride; boiling point: 153°–155° C. at 0.2 mbar.

EXAMPLE 2

Cyclohexanecarboxylic acid anhydride 100 g of trimethylsilyl cyclohexanecarboxylate (0.5 mol) and 73.3 g of cyclohexanecarboxylic acid-chloride (0.5 mol) were warmed to 140° C. in a 250 ml three-necked flask and the trimethylsilyl chloride formed was distilled off in the course of 40 minutes. The residue was distilled off in vacuo. Yield 114 g (≅96% of theory) of cyclohexanecarboxylic acid anhydride; boiling point: 128° to 131° C. at 0.2 mbar.

EXAMPLE 3

4,4'Dichloro-benzoic anhydride 114.3 g of trimethylsilyl 4-chlorobenzoate (0.5 mol) and 87.8 g of 4-chlorobenzyl chloride (0.5 mol) were mixed in a 250 ml three-necked flask equipped with a stirrer, a thermometer and distillation bridges, and the mixture was warmed to 150° C. Only a small amount of trimethylsilyl chloride was split off. After the addition of 0.1 g of zinc chloride, the trimethylsilyl chloride must be distilled off vigorously at this temperature. After the reaction was complete, the residue was recrystallized from chlorobenzene. Yield: 139 g (≅94% of theory) of 4,4'-dichlorobenzoic anhydride; melting point: 195° C.

The carboxylic acid anhydrides (I) listed in Table 1 below could also be prepared analogously to Examples 1 to 3:

TABLE 1

| Example No. | Carboxylic acid anhydride (I) | Yield | Boiling point (b.p.); melting point (m.p.) |
|---|---|---|---|
| 4 | $(CH_3-CO-)_2O$ | 85% | b.p.: 138–140° C. |
| 5 | $(CH_3-CH_2-CO-)_2O$ | 96% | b.p.: 168–169° C. 67.5° C./24 mbar |
| 6 | $[(CH_3)_3C-CO-]_2O$ | 95% | b.p.: 83–85° C./20 mbar |
| 7 | [2,5-dichlorobenzoyl]$_2$O | 87% | b.p.: 208–211° C./ 0.266 mbar m.p.: 107–109° C. |
| 8 | [4-nitrobenzoyl]$_2$O | 86% | m.p.: 186–190° C. |
| 9 | [2-furoyl]$_2$O | 84% | b.p.: 153–168° C./0.4 mbar m.p.: 70–72° C. (gas chromatography: 99% purity) |
| 10 | [4-methoxybenzoyl]$_2$O | 95% | m.p.: 97–99° C. |
| 11 | 4-CH$_3$O-C$_6$H$_4$-COOCO-C$_6$H$_4$-4-Cl | 93% | m.p.: 167–169° C. from chlorobenzene) |

It is understood that the specification and examples are illustrative but not limitative of the present invention and that other embodiments within the spirit and scope of the invention will suggest themselves to those skilled in the art.

I claim:

1. A process for the production of a carboxylic acid anhydride of the formula $$R-CO-O-CO-R^1$$

in which

R and R$^1$ each independently is an optionally substituted alkyl group having 1 to 18 carbon atoms, an optionally substituted cycloalkyl group having 3 to 12 carbon atoms, an optionally substituted aryl group, or an optionally substituted 5-membered or 6-membered heterocyclic radical which additionally can be fused to a benzene ring,
comprising reacting a trimethylsilyl carboxylate of the formula R—CO—OSi(CH$_3$)$_3$ with a carboxylic acid-halide of the formula

R$^1$—CO—X in which
X is a halogen atom, at a temperature between about 20° and 250° C.

2. A process according to claim 1, wherein the reaction is carried out at a temperature between about 50° and 200° C.

3. A process according to claim 1, wherein the reaction is carried out in the presence of a catalyst.

4. A process according to claim 3, wherein the catalyst is a Lewis acid.

5. A process according to claim 1 wherein the reaction is carried out in the presence of a diluent.

6. A process according to claim 5, wherein the diluent is an inert organic solvent.

7. A process according to claim 1, wherein trimethylsilyl halide is formed as a by-product in the course of the reaction and is distilled off continuously from the reaction mixture at the rate at which it is formed.

8. A process according to claim 1 in which R and R$^1$ each independently is an alkyl group having 1 to 4 carbon atoms and optionally substituted by a substituent selected from alkoxy having 1 to 4 carbon atoms, carbalkoxy having 1 to 4 carbon atoms in the alkoxy group, nitro, cyano, fluorine, chlorine, bromine and iodine; a cycloalkyl group which is optionally substituted by a substituent selected from alkyl, alkoxy, or carbalkoxy, each having up to 4 carbon atoms, nitro, cyano, fluorine, chlorine and bromine and which has 5 or 6 carbon atoms in the ring system; a phenyl or naphthyl group which is optionally substituted by alkyl, alkoxy or carbalkoxy, each having up to 4 carbon atoms, nitro, fluorine, chlorine and bromine; or a 5-membered or 6-membered heterocyclic radical which is optionally substituted by substituent selected from alkyl, alkoxy or carbalkoxy, each having up to 4 carbon atoms, nitro, cyano, fluorine, chlorine and bromine and contains 1 to 3 oxygen, sulphur and/or nitrogen atoms in the ring and additionally can be fused to a benzene ring.

9. A process according to claim 1, in which X is a fluorine atom.

10. A process according to claim 1, in which X is a chlorine atom.

11. A process according to claim 1, wherein R is phenyl or tert.-butyl.

12. A process according to claim 1, wherein R$^1$ is phenyl or tert.-butyl.

13. A process according to claim 8, wherein X is a fluorine or chlorine atom, the reaction is carried out at a temperature between about 50° and 200° C. in the presence of a Lewis acid as catalyst, and trimethylsilyl fluoride or chloride is formed as a by-product in the course of the reaction and is distilled off continuously from the reaction mixture at the rate at which it is formed.

* * * * *